United States Patent [19]
Williams et al.

[11] Patent Number: 4,665,911
[45] Date of Patent: May 19, 1987

[54] INTERMITTENT SUPPLEMENTAL OXYGEN APPARATUS AND METHOD

[75] Inventors: W. Samuel Williams, Carefree; David L. Hadley, Gilbert; Narciso F. Macia, Tempe, all of Ariz.; Alvin S. Blum, Fort Lauderdale, Fla.

[73] Assignee: Electro-Fluidics, Boca Raton, Fla.

[21] Appl. No.: 554,904

[22] Filed: Nov. 25, 1983

[51] Int. Cl.$^4$ .............................................. A61M 16/00
[52] U.S. Cl. .......................... 128/204.21; 128/204.23
[58] Field of Search ..................... 128/204.18, 204.24, 128/204.25, 204.27, 205.24, 204.21, 204.23; 137/624.14, 624.15; 253/200 R

[56] References Cited

U.S. PATENT DOCUMENTS

| | | | |
|---|---|---|---|
| 3,067,760 | 12/1962 | Haverland et al. | 137/624.14 |
| 3,385,294 | 5/1968 | Sabatnie et al. | 128/204.21 |
| 3,400,712 | 9/1968 | Finan | 128/204.21 |
| 3,472,225 | 10/1969 | Burns | 128/204.24 |
| 3,500,826 | 3/1970 | Haire | 128/204.21 X |
| 3,598,116 | 8/1971 | Peters | 128/204.24 X |
| 3,662,751 | 5/1972 | Barkalow et al. | 128/204.25 |
| 3,788,313 | 1/1974 | Arp et al. | 128/204.21 |
| 3,889,669 | 6/1975 | Weigl | 128/204.18 |
| 3,910,303 | 10/1975 | Rydberg | 137/624.14 X |
| 3,976,064 | 8/1976 | Wood et al. | 128/204.21 |
| 3,981,301 | 9/1976 | Warnow et al. | 128/204.24 |
| 4,206,754 | 6/1980 | Cox et al. | 128/204.21 |
| 4,215,681 | 8/1980 | Zalkin et al. | 128/204.21 |

FOREIGN PATENT DOCUMENTS

| | | | |
|---|---|---|---|
| 835192 | 5/1960 | United Kingdom. | |
| 2079984 | 1/1982 | United Kingdom | 128/204.21 |

OTHER PUBLICATIONS

"XIII World Congress on Diseases of the Chest", International Academy of Chest Physicians and Surgeons, Kyoto International Conference Hall, Jul. 7, 1978.

*Primary Examiner*—Glenn Caldarola
*Attorney, Agent, or Firm*—Alvin S. Blum

[57] ABSTRACT

A method and apparatus for intermittent administration of supplemental oxygen to chronic obstructive pulmonary disease patients programmed for specific oxygen needs for each patient. Patient's arterial blood oxygen level is measured while supplying oxygen to determine the time required to reach a desired level and it is again measured without supplemental oxygen to determine the time required to diminish to a second, lower particular level. These two time intervals are applied as a program to apparatus connected to a supply of oxygen having valve and time controls to provide a regulated flow of supplemental oxygen to a nasal cannula for a preset time and to shut off the flow for a preset time sequentially and repetitively. The apparatus is powered by the energy of the gas itself either directly by gas powered controls and valves or indirectly with electrically powered controls and valves with gas power operating an electric generator to supply the necessary electrical power.

16 Claims, 7 Drawing Figures

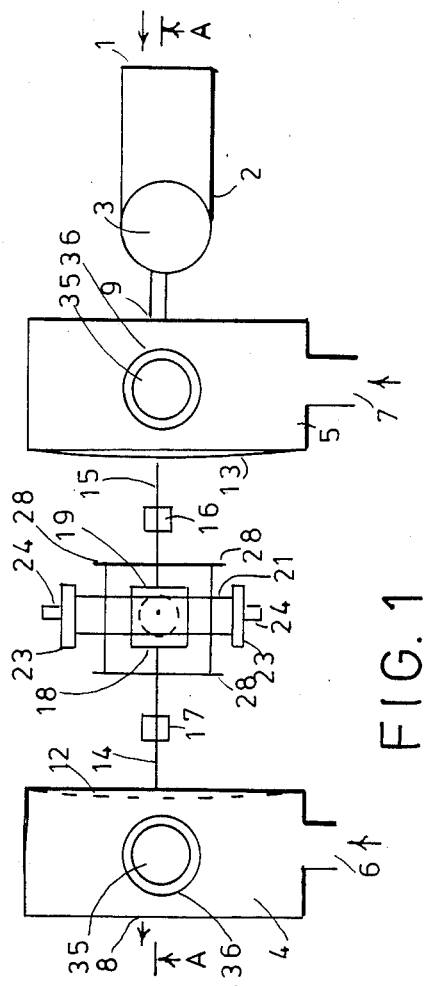
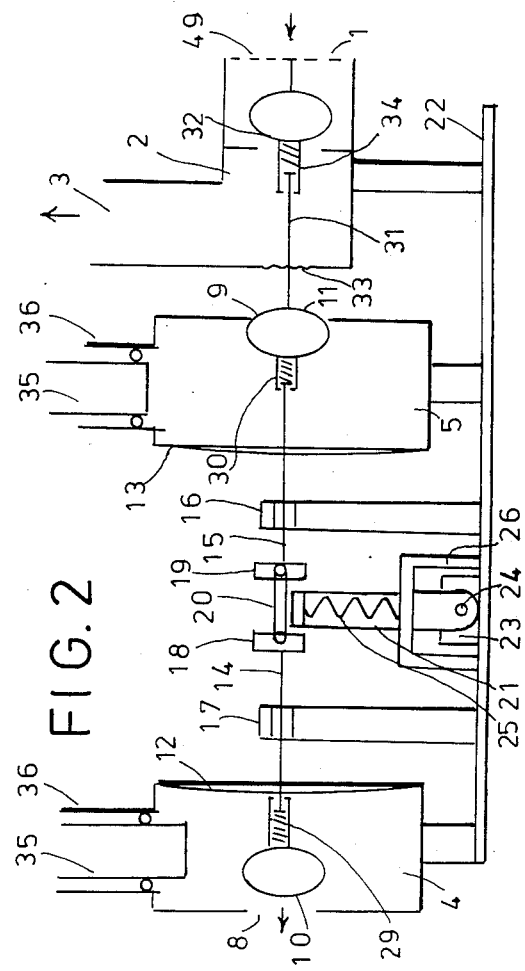
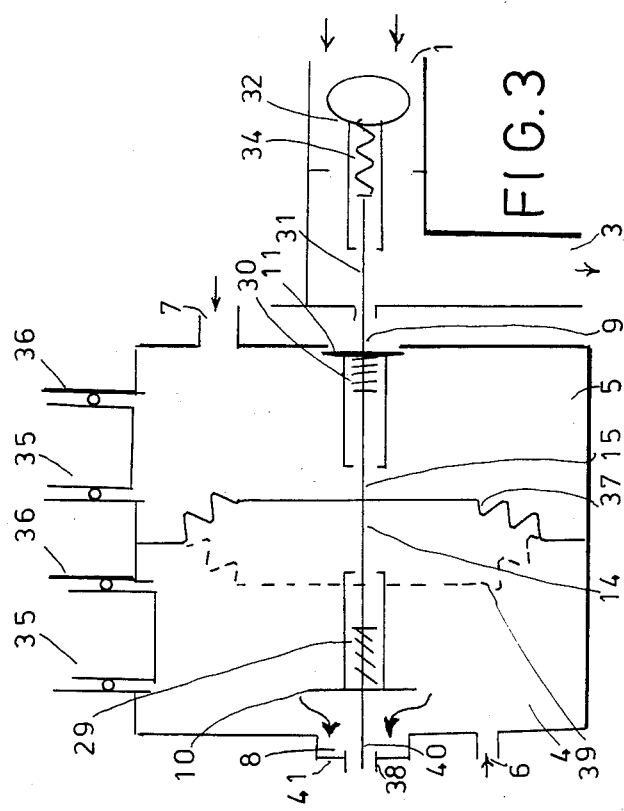
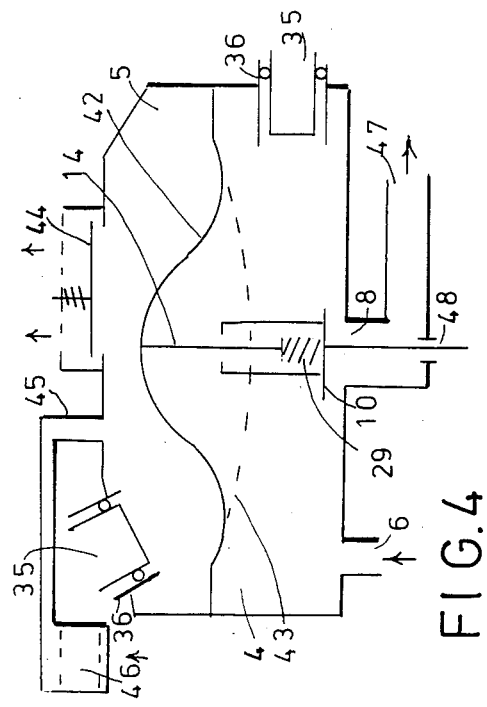
FIG. 1
FIG. 2
FIG. 3
FIG. 4

INTERMITTENT SUPPLEMENTAL OXYGEN APPARATUS AND METHOD

BACKGROUND OF THE INVENTION

This invention relates to systems for supplying supplemental oxygen to a patient intermittently with the supply on for a predetermined time interval extending over a plurality of respiratory cycles and the supply off for a plurality of respiratory cycles, where the on and off times are preset based upon prior measurements of the patient's oxygen requirements.

The rate of disability from chronic obstructive lung disease (C.O.L.D.) has been increasing. Such patients have inadequate pulmonary gas exchange resulting in inadequate oxygenation of blood as it passes through the lungs. Inadequate oxygenation of the blood, and thereby the body tissues accounts for the disabling effects of the disease. It has been demonstrated, that continuous administration of supplemental oxygen by nasal cannula overcomes the functional disability and greatly improves the quality of life as well as prolonging life. It is now common practice for ambulatory patients to carry a liquid oxygen cannister supply which weighs nine pounds and lasts approximately 3-4 hours. A usual oxygen supply costs hundreds of dollars a month.

BRIEF SUMMARY OF THE INVENTION

Restricted mobility, activity and costs of this therapy can be reduced by intermittent oxygen therapy. This intermittent oxygen therapy can replace continuous oxygen therapy because of the unusual physiological nature of C.O.L.D.

C.O.L.D. destroys lung tissue and impairs the lung's blood supply. As a consequence, the gas exchange behavior of the lungs is impaired, resulting in diminished oxygenation of the arterial blood. When such patients breathe air enriched with supplemental oxygen, the partial pressure of oxygen within the lungs is increased. This improves the transfer of oxygen from the lung to the blood and increases the oxygen content of the blood.

When oxygen administration is discontinued and the patient is returned to breathing room air, the arterial oxygen content remains elevated for a varying period. The oxygen content only very slowly returns to that value obtained while breathing room air. Depending upon the degree of pulmonary abnormalities, this may require 20-25 minutes. By contrast, patients with previously normal lungs requiring oxygen therapy (example: patients with heart failure), will promptly return to the value obtained while breathing room air (3-5 minutes).

Since many C.O.L.D. patients maintain an adequate level of arterial blood oxygenation for a prolonged period following cessation of oxygen administration, advantage is taken of this response by discontinuing oxygen therapy while the oxygen level still remains at an appropriate value. Discontinuation during this time conserves oxygen. When the arterial oxygen saturation has decayed to a pre-determined lower value, oxygen administration is re-started, and continues until appropriate oxygenation of the blood is re-established. At this time administration is again discontinued. These cycles repeat on a continuous basis administering $O_2$ intermittently to maintain adequate arterial oxygenation.

C.O.L.D. patients have many abnormally enlarged spaces within their lungs that are slowly ventilated and have a very poor blood supply. These areas act as "internal reservoirs" which store air enriched with oxygen when such is being breathed. When regular air breathing is resumed, these areas transfer the oxygen enriched air to adjacent areas of the lungs with a better blood supply and act as a source of continued oxygenation of the blood for some time after supplemental oxygen has been discontinued.

Recently developed sophisticated instrumentation (Hewett-Packard Ear Oximeter, Model 47201A) allows for the continuous determination of arterial oxygen saturation—an index of oxygen content. This is a painless, non-invasive method. Determination of the time to obtain appropriate oxygenation at a selected flow of oxygen (usually 2L/Min) establishes the "on" time of oxygen administration. After this value is determined, a recording is made of the rate of decline in the oxygen saturation after oxygen has been discontinued. This defines the "off" time. These 3 parameters, "on" time, "off" time, in minutes, and the flow rate, L/Min, are entered into the oxygen delivery system of the invention. This system uses the energy of the oxygen supply to control the flow rate and timing sequences. There is no external power source required. The entire sequential system is controlled by the energy generated from the compressed oxygen source. The unit is interfaced between the patient and any conventional oxygen source (gas or liquid). Oxygen is conveyed from the unit to the patient by plastic tubing terminating in the nasal prongs. Thusly, the system continuously and automatically delivers oxygen, intermittently, to the subject, as required, conserving at least 50% of the oxygen supply when compared to prior art continuous systems.

It is an object of the invention to provide a method for intermittent oxygen therapy for a C.O.L.D. patient which is supplemental to the patient's normal room air intake. This is generally delivered via a loosely fitting nasal cannula without altering the pressure relationships within the respiratory tract. When the patient inhales while gas is supplied to the cannula, the volume of gas inhaled is not changed, only the concentration of oxygen is increased. This is in contrast to respirators and ventilators which form a closed circuit with the respiratory tract and provide alternate pressure and suction to move all gas into and out of the lungs at different portions of each respiratory cycle. It is an object of the invention to provide a system which cyclically administers oxygen during an ON interval extending over a plurality of respiratory cycles followed by an OFF period extending over a plurality of respiratory cycles wherein the intervals are independently adjustable and are predetermined from prior measurements of the patient's requirements for such therapy. These and other features, objects and advantages will become more apparent from the following description and drawings of preferred embodiments of the invention wherein:

BRIEF DESCRIPTION OF THE DRAWINGS

FIG. 1 shows a top view of a gas powered moving part oscillator embodiment of the invention.

FIG. 2 shows a side sectional view through plane A—A of FIG. 1.

FIG. 3 shows, in sectional view, a gas powered moving part oscillator embodiment employing a single diaphragm.

FIG. 4 shows, in sectional view, moving part oscillator embodiment with a single diaphragm employing room air in one chamber.

FIGS. 1, 2, 3 and 4 show moving part oscillator embodiments of the invention.

These embodiments employ two chambers each closed by a flexible diaphragm which fill and pressurize alternately to actuate a toggle mechanism by displacement of the diaphragms. One chamber serves as an ON timer and the other as an OFF timer. Time interval adjustment is by adjustment of chamber volume which has advantages over rate limiting orifices for timing. May be powered by oxygen supply and may be vented to patient oxygen delivery line to conserve gas and eliminate external power requirements. The to and fro toggling motion is coupled to an ON/OFF valve to provide the prescribed periods of supplemental oxygen supply. It may include a "sticky valve" mechanism to simplify structure and function. This takes advantage of the pressure in a filled chamber holding a valve closed while toggle is slowly being loaded, so that the snap action of the toggle is necessary to crack the valve. FIG. 1 and 2 illustrate an embodiment using one of the many toggle means well known to the prior art which is driven alternately by the alternately filling chambers by the bulging of their diaphragm walls. This motion is tied to the ON/OFF gas valve in the system to be controlled. FIG. 3 and 4 show embodiments wherein the two chambers share a common diaphragm. The diaphragm is a warped surface having inherent toggle action (bistable form).

FIG. 1 shows a top view of an embodiment of the invention.

FIG. 2 shows a side sectional view through plane A—A of FIG. 1. Gas to be controlled flows into gas control valve 2 at inlet 1 and out of outlet 3. The same gas enters chambers 4 and 5 at inlets 6 and 7 respectively and leaves through outlets 8 and 9 respectively. Outlet valve 10 of chamber 4 is open so that gas escapes through outlet 8 while outlet valve 11 of chamber 5 is closed, preventing gas escape through outlet 9 so that incoming gas is pressurizing the chamber, causing diaphragm 13 to bulge outwardly. Drive rod 15, sliding in sleeve support 16 is connected to center of diaphragm 13. Its free end is a rectangle 19 which slideably engages rod 20 which is a rod bent into a rectangular shape and fastened atop U shaped member 21 which is pivotally supported on base plate 22 by brackets 23 at pivots 24. Outward bulging of diaphragm 13 has forced rectangular end 19 of drive rod 15 against rod 20, causing U shaped member 21 to rotate counter clockwise around pivots 24, thereby compressing toggle spring 25 against stand 26. The toggle mechanism 27 is shown in the vertical or metastable or loaded position. Another increment of gas in chamber 5 will cause an incremental motion of rod 15. This will move member 21 to the left just enough past the vertical position so that the spring will be able to push and move member 21 forcefully to the left with the energy stored up in the spring by the gradual pressure build up and diaphragm movement. Stops 28 on stand 26 limit the range of motion of member 21. Rod 15 extends through diaphragm 13 into chamber 5 and into sleeve of gas outlet valve 11, connecting to it by tension spring 30, which is trying to pull the valve open by stretching the spring. However, this is a "sticky valve" which is designed to remain closed during this slow outward motion of rod 15. This is necessary for the toggle action, otherwise valve 11 would gradually open and spill gas at outlet 9, preventing further counterclockwise motion of the toggle mechanism. When valve 11 initially closed, it was from the snap clockwise motion of the toggle in the last cycle. It was forced closed by the end of rod 15 pushing the spring 30 up against the base of valve 11 forcing it against the outlet 9. This condition applied while the chamber filled with gas until pressure build up caused diaphragm 13 to bulge. This started the outward movement of rod 15, but by the time it had moved enough to put tension on spring 30 in the sleeve of valve 11, pressure inside chamber 5 and on inside surface of valve 11 was so much greater than outside at outlet 9 that it held it closed with a force equal to the difference in pressure times the area. This is enough to resist the tension of relatively weak spring 11. Therefore valve 11 remains closed until the motion of the toggle passes the mid point, whereupon the expanded end of rod 15 engages the constricted end of the sleeve of valve 11 and pulls it open. Then spring 30 can pull the valve in to the relative positions of valve and rod seen on the opposite side with rod 14 and valve 10. This pressure release deflates chamber 5 and leaves valve 11 open so that the chamber 5 cannot repressurize.

Figure 5:
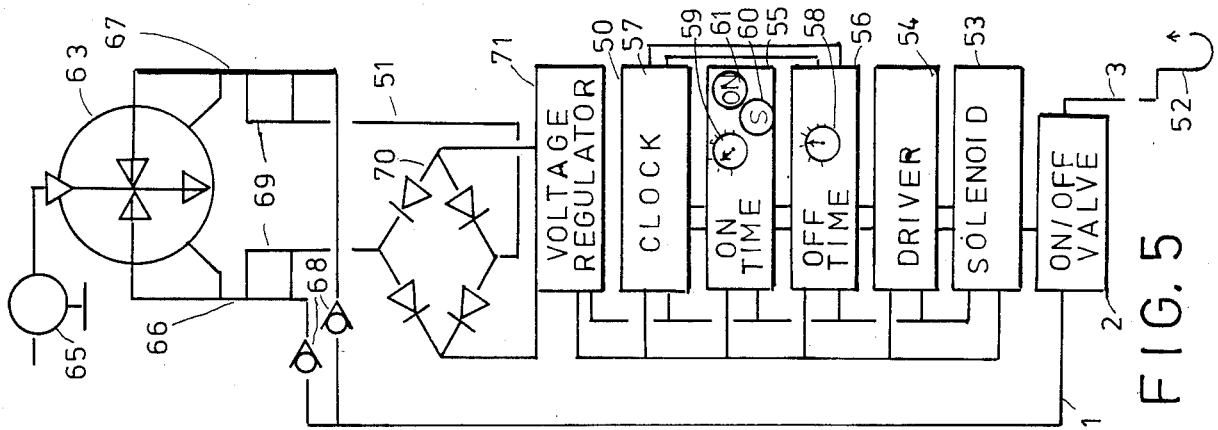
FIG. 5 is a diagram of an electrical embodiment of the invention with gas powered electric generator.

When member 21 snaps counterclockwise by the toggle action of spring 25, rod 20 acting on rectangular end 18 of rod 14 pushes valve 10 closed. The sliding rectangular linkages of ends 18 and 19 of rods 14 and 15 with rod 20 is designed to transform the arcuate motion of member 21 into translatory motion of the rods. Sliding supports 16 and 17 further this process. Now chamber 4 will fill since its outlet 8 is now closed and outlet 9 of chamber 5 is open. Diaphragm 12 will now reverse from position shown and will bulge outwardly, and member 21 will slowly move from its position against stops 28 to the vertical position while storing energy in the compression of toggle spring 25. This alternating process is coupled to the gas valve 2 by connecting rod 31 which is connected to valve 11. Connecting rod 31 passes through the wall of gas valve 2 through a diaphragm gas seal 33 into the sleeve of valve 32. It is coupled to valve 32 by tension spring 34 so that successful operation will not be so critically dependent on exact dimensions. Valve 32 is supported distally by archimedes spring 49.

The time that this device will dwell in either of the two bistable states is determined by the time it takes to fill each chamber to a certain pressure. Since one chamber is venting while the other is filling, each chamber's rate is independent of the other's rate. The rate can be separated into two factors (a) the rate of gas flow in and (b) the volume to be filled. (a) will be influenced by inlet gas pressure and flow impendance. Usual practice is to employ a restrictive orifice which is adjusted to regulate flow rate. The instant invention provides a second means of adjustment more useful for long time intervals and low flow rates by adjustment of factor (b), the total volume to be filled. Pistons 35 fit slideably into leak tight cylinders 36. By adjusting the positions of the pistons 35 within cylinders 36 by suitable adjusting means, one can vary the total volumes of chambers 4 and 5, and thereby their filling times. If the chamber volume is doubled, the time required to fill to the same pressure will be doubled. At low flow rates, this can be more useful than limiting orifices which require very small holes that are unstable and easily contaminated. The system is very economic of gas since it uses volume and not flow for control.

FIG. 3 is an example of the use of a warped surface as the bistable or toggle element. Membrane 37 forms a common, displaceable diaphragm for the chambers 4 and 5. It is formed of a springy material and is a warped surface having a plurality of annular corrugations. Membrane 37, by virtue of its having two stable positions and a metastable central position, serves as the toggle element as well as the common diaphragm. Gas entering chamber 5 through inlet 7 builds up pressure against membrane 37 because outlet 9 is closed by valve 11. As pressure builds in chamber 5, the corrugations are compressed as the diaphragm 37 moves to the midplane. When membrane 37 advances far enough beyond the midplane, it will snap to the reverse position 39 shown in phantom. Rods 14 and 15 are attached at the center of diaphragm 37. Sleeve support 38 may guide position of valve 10 with guide rod 40. Sleeve support 38 is held by spider 41 which does not obstruct gas flow. The gas exhausted at outlets 8 and/or 9 may be connected to patient delivery tube to conserve gas.

The system employs the "sticky valves" 10 and 11 and controls ON/OFF valve 2 in the gas line by connecting rod 31 tied to valve 11 as in the description of FIGS. 1 and 2. Time intervals are adjusted by altering positions of pistons 35 in cylinders 36 to change total volume.

The embodiment of FIG. 4 employs the common membrane 42 which is a warped surface such as a section of the surface of a spheroid, which has the stable position 43 shown in phantom. Gas supply flows in at 6 and out at 8. When "sticky valve" 10 is closed, pressure in chamber 4 builds up and membrane 42 eventually buckles into chamber 5 in the alembic shape shown. Air trapped in chamber 5 is exhausted out spring loaded check valve 44. This relatively abrupt motion extends far enough to pull open "sticky valve" 10, which assumes position shown as tension spring 29 pulls the valve onto drive rod 14.

Gas pressure now escapes from chamber 4 through outlet 8, stopping forward motion of membrane 42 and check valve 44 closes. Membrane 42 is of such shape that it now attempts to springably return to its stable position 43 in chamber 4. This motion is restricted by the vacuum produced in chamber 5. Room air is slowly drawn into chamber 5 through filter 46 and capillary tube 45, thereby slowly releasing forces on membrane 42 which has the property of suddenly snapping into the relaxed position 43 when a certain critical point is reached in its motion, thereby providing the toggle like action which abruptly closes valve 10 and cuts off the flow of gas at tube 47. This system saves gas by only using it in chamber 4. When gas tube 47 is the gas being controlled, valve 10 also serves as the ON/OFF valve of the system. Connecting rod 48 may operate a two position flow rate controller so that the rate of gas flow when valve 10 is open is the rate required by the ultimate gas use and the rate of gas flow when valve 10 is closed is that required for pressurizing chamber 4. Volume adjusting pistons 35 in cylinders 36 control the on/off intervals independently.

The membrane 37 of FIG. 3 may alternatively be of composite construction. A center flat disc may be connected to an outer, concentric flat annulus by a plurality of flat compression springs. The whole may then be sandwiched between two resilient membranes to provide the gas tight properties. The springs are long enough so that when the disc and annulus are coplanar, the springs are compressed.

The embodiment of FIG. 5 includes an electrically operated on/off oxygen control apparatus 50 and a piezoelectric generator system 51. ON/OFF valve 2 controls oxygen supply to nasal cannula 52. Solenoid 53 closes valve 2 when energized. When deenergized, solenoid/valve combination is spring loaded so as to remain open as a failsafe function. Clock 57 includes a frequency divider and crystal oscillator which puts out a pulse at timed intervals. For illustrative purposes, we will say the clock puts out a pulse every minute and the prescription or required program calls for 5 minutes ON and 9 minutes OFF. Clock pulses are fed to OFF timer 56 and ON timer 55. These timers are preset digital counters which count up the clock pulses until the number indicated on the time interval adjust dial is reached. OFF adjust dial 58 is set at 9 and ON adjust dial 59 is set at 5. Whenever START button 60 is pressed, counters reset to zero and an ON interval begins as counter in ON timer 55 is enabled and clock pulses are counted until 5 have been counted. At that time, both counters reset to zero, ON counter is disabled, OFF counter is enabled, and OFF timer 56 sends an enable signal to driver circuit 54, which continues as long as OFF timer is counting. Driver circuit 54, when enabled, operates solenoid 53, which closes valve 2. Driver 54 may contain an optoelectronic isolator and solid state relay to control the high current inductive load of the solenoid with the low power timing circuit. When OFF timer 56 reaches a count of 9, both counters reset, ON timer is enabled and OFF timer is disabled. Solenoid is deactivated and valve 2 opens and gas flows. The ON time interval now begins and this cycle repeats. A continuous ON/OFF switch 61 is provided. When ON, this switch disables time controls and valve 2 remains open to provide continuous oxygen when required.

Electric power lines 62 provide electric power to time control apparatus 50 from piezoelectric generator system 51, which includes a conventional wall action fluidic oscillator 63 fed by the oxygen supply input line 64 from pressure regulator 65. Action of the oscillator results in the flow from input line 64 alternately appearing at first output line 66 and then second output line 67. These outputs are fed to a common gas line 1 which eventually feeds to the patient cannula 52. Gas diodes 68 prevent pressure feedback. Piezoelectric elements 69 responsive to pressure changes in gas output lines 66 and 67 with an electrical potential. The gas pressure oscillations thereby generate an alternating electric current which is rectified in rectifier circuit 70 and stabilized and regulated in voltage regulator circuit 71 before feeding into power lines 62 to time control mechanism 50.

Figure 6:
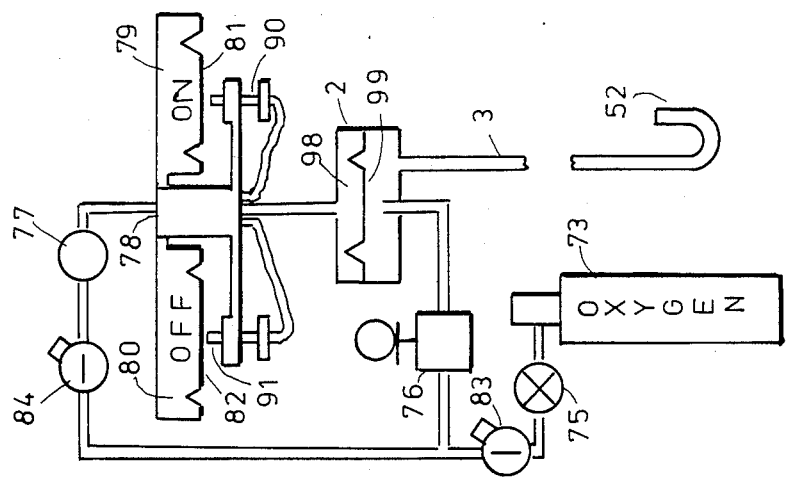
FIG. 6 is a diagram of a fluidic control embodiment of the invention.
Figure 7:
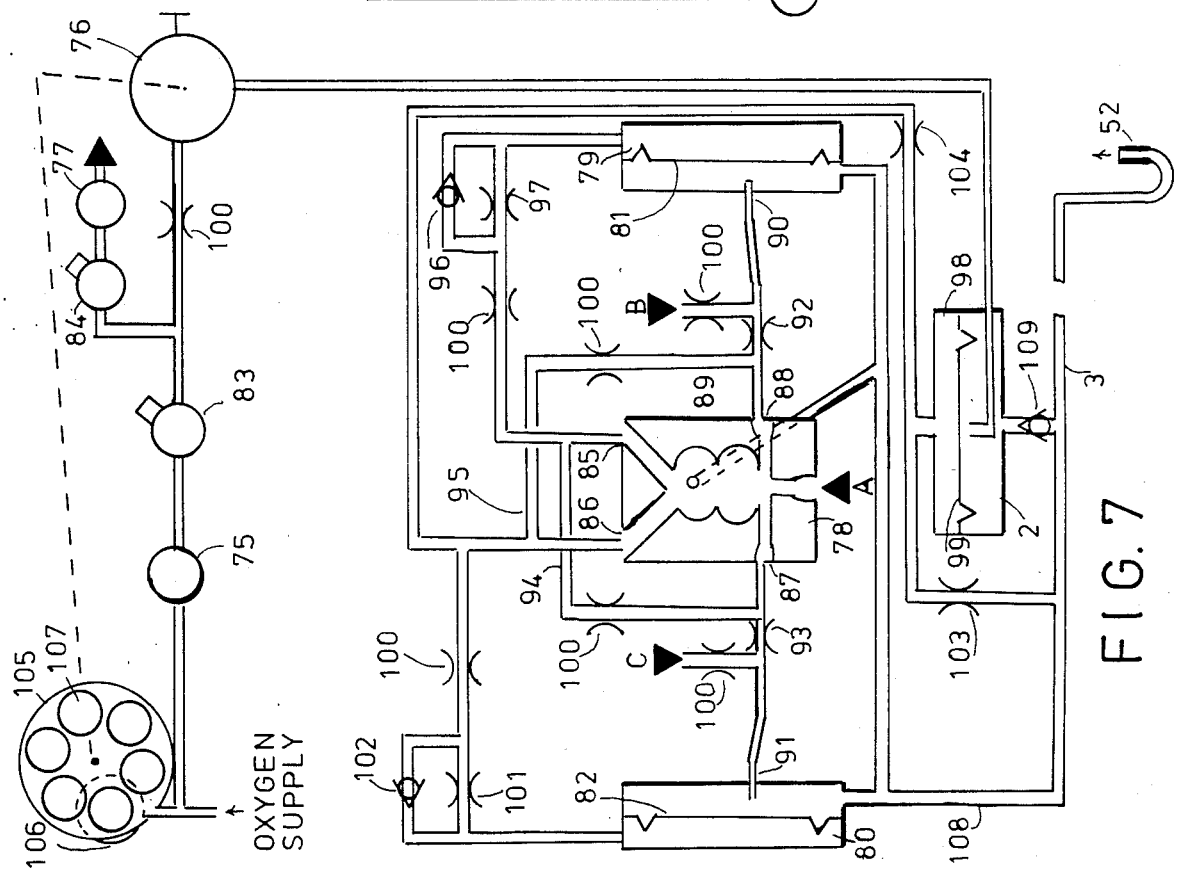
FIG. 7 is a detailed diagram showing the positive feedback proportional amplifier flip flop timing control element of FIG. 6.

FIGS. 6 and 7 are diagrammatic views of an embodiment of the invention employing a very low frequency fluidic flip flop oscillator and very low gas flow rates. Conventional fluidic oscillators require substantial gas flow rates and cannot readily operate at the low frequencies necessary for this application where intervals between a flip and a flop may vary between thirty seconds and twenty minutes. Flow rate to a patient is generally around 2L/min. and only a small portion of this flow is available for fluidic control. The invention achieves these unique objectives by the use of fluidic proportional amplifier 78 using approximately 0.1

L/min. that alternately supplies flow to two timing chambers; an ON chamber 79 and an OFF chamber 80. These chambers are closed by flexible metal diaphragms 81 and 82 respectively. Oxygen from a home, or hospital stationary supply, or a portable liquid gas supply, or the tank 73 shown, passes through pressure regulator 75, then branches to a first branch through pressure regulator 75, then branches to a first branch through flow rate selector valve 76 to ON/OFF gas valve 2 to outflow line 3 to patient cannula 52. A second branch passes through filter 77 to three inputs A,B,C in timing control circuit. Gas line connections between the filter and the three inputs are indicated by the closed triangle symbols. ON/OFF toggle valve 83 shuts off oxygen supply. Continuous/Intermittent toggle valve 84 shuts off flow to timer circuit, allowing valve 2 to remain ON continuously. A proportional fluid amplifier 78 with positive feedback is used as the memory element. When oxygen supply to the timing circuit is first applied, the flow into inlet A is deflected to outlet 85, which then flows into ON timing chamber 79, increasing its pressure, which deflects diaphragm 81 outwardly. A portion of the flow from outlet 85 is fed back via line 94 to ON control port 87. This pressure at ON control port 87 causes gas flow from A to be directed to outlet 85. This is the positive feedback which stabilizes this condition. Vent 89 feeds into collecting line 108. This is the first of the two stable states of the oscillator. Gas input at B flows out ON nozzle 90 and is connected through resistor 92 to OFF control port 88. Gas input at C flows out OFF nozzle 91 and is connected through resistor 93 to ON control port 87. While flow out the nozzle is unobstructed by a diaphragm, these flows transmit only a low pressure to their control ports. Chamber 79 continues to fill with gas and diaphragm 81 distends until it obstructs the outflow at ON nozzle 90. When flow out nozzle 90 is obstructed, this "flapper-nozzle" action causes a high pressure to be transmitted from input B to OFF control port 88 which forces the flow from outlet 85 to outlet 86. A first portion of the gas flow from outlet 86 is fed back via line 95 to control port 88. This is the positive feedback which stabilizes this second stable state of the oscillator. ON chamber 79 now empties. Diode 96, shunting resistor 97, enables chamber 79 to empty much faster than it fills. A second portion of the gas flow of outlet 86 is directed to pressurize chamber 98 of outlet valve 2, causing its diaphragm 99 to close off the gas flow to the patient line 3. A third portion of the gas flow of outlet 86 is directed to OFF timing chamber 80 which fills with gas as diaphragm 82 distends until it obstructs outflow of gas at OFF nozzle 91. When flow out nozzle 91 is obstructed, this flapper-nozzle action causes a high pressure and flow to be transmitted from input C to ON control port 87, which forces the flow from outlet 86 to outlet 85 which terminates the OFF cycle and begins another ON cycle. Because chamber 98 of valve 2 no longer has pressure, it empties to outlet line 3 as diaphragm 99 retracts and valve 2 opens. The distance between each nozzle and its diaphragm may be adjusted to increase or decrease the ON time and the OFF time independently, and the adjustment may be indicated by a calibrated dial. Fluid resistors 100 comprised of capillary tubing of different lengths and diameters provide appropriate gains to make the circuit bistable. Resistors 97 and 101 determine the flow rate to the chambers. Check valves 96 and 102 provide quicker emptying of the chambers. Resistors 103 and 104 form a bridge circuit to decrease the pressure to the outlet valve. Collecting line 108 collects gas vented from time control circuits and feeds it to patient line 3, isolated by valve 109, to conserve gas.

Flow Rate Selector Valve

Different gas flow rate settings for supply to the patient are obtained by inserting different size orifices in the gas stream. Rotation of the flow rate selector valve 76 selects and inserts into the gas line a particular orifice for a particular flow rate (at a given pressure). Coupled to the selector valve mechanism 76 is a circular transparent plate 105, bearing a plurality of dial faces 107 inscribed thereon. There is one dial face corresponding to each orifice. A pressure guage 106 in the gas line indicates pressure in the tank 73 which indicates the amount of gas remaining. The circular plate 105 is so positioned relative to pressure gauge 106 that a dial face 107 corresponding to the particular orifice currently inserted into the line by flow rate selector valve 76 is superimposed directly over the face of the pressure gauge. This dial face is calibrated in minutes or hours of time remaining so that the pressure indicating needle now points, not to a number of pounds per square inch, but to a number of minutes which that amount of gas will supply at that particular flow rate. This would apply to continuous flow. For intermittent flow, this time should be multiplied by the factor:

Time ON + Time OFF/Time ON

A number of different embodiments of the apparatus of the invention have been illustrated. In performing the method of the invention, the supplemental oxygen breathing requirements of the patient must first be determined. This step is not illustrated. In this step, the patient's blood oxygen saturation is measured, such as by an earpiece oximeter. This provides an indication of the degree of oxygen saturation of the blood hemoglobin by optically measuring the ratio of oxygenated hemoglobin to deoxygenated hemoglobin. Supplemental oxygen is administered at a particular flow rate by nasal cannula and a stopwatch is used to measure the time required to reach a desired upper level of oxygen saturation as indicated by the oximeter. The oxygen flow is then stopped, and the time required to reach an acceptable lower level of oxygen saturation is measured. These time interval measurements may be repeated at different flow rates and under different patient conditions, (e.g. upright and recumbent), until a suitable setting of the apparatus for that particular patient's supplemental oxygen requirements have been established. These settings of flow rate and time intervals may be made to the apparatus and the prescribed program applied to the patient to test the efficacy of the prescription on blood oxygen levels, and to make any necessary final corrections thereto.

The patient may then use the apparatus which will automatically provide the prescribed oxygen therapy. Testing and resetting of the apparatus may be repeated from time to time as the patient's condition warrants. Usual setting may be around 2L/min., 2 minutes ON, 5 minutes OFF, but there are great individual variations.

The above disclosed invention has a number of particular features which should perferably be employed in combination although each is useful separately without departure from the scope of the invention. Inasmuch as the invention is subject to many variations, modifications, and changes in detail, it is intended that all matter described above be interpreted as illustrative and not in a limiting sense.

We claim:

1. Apparatus for conserving oxygen by providing, sequentially and repetitively, an ON time period and OFF time period of measured flow of supplemental oxygen gas from an oxygen supply conduit and through a delivery conduit adapted for delivering said gas to a spontaneously breathing patient without substantially obstructing said patient's normal ambient air intake for improved function in certain disorders, as exemplified by chronic obstructive pulmonary disease, according to a program based upon such patient's characteristics relative to saturation time and desaturation time in said patient's use of such oxygen, comprising in combination:

automatically operated on/off valve means connected in said supply conduit to permit the flow of oxygen therethrough for a first, or ON time period and to provide said supplemental oxygen to said patient substantially at atmospheric pressure and without substantially obstructing ambient air intake and to prevent said flow for a second, or OFF time period to conserve said oxygen gas;

time control means operatively connected to said valve means to actuate said valve means in accordance with said program, including independently adjustable ON time interval adjustment means and OFF time interval adjustment means, wherein each said time interval is independent of said patient's respiratory cycle, extends over a plurality of respiratory cycles, and is preset;

time clock means operatively connected to said time control means to provide time period information to said time control means;

and means to operate said valve means and said time control means with energy derived from the expanding and flowing oxygen gas.

2. Apparatus of claim 1, including gas flow regulator means connected to said supply conduit to control the flow rate of oxygen therethrough and to the patient.

3. Apparatus of claim 1, wherein said valve means and said time control means are electrically operated, and including electricity generating means operatively connected in said oxygen conduit to provide electric power to said valve means and said said time control means.

4. Apparatus of claim 3, wherein said electricity generating means includes fluidic oscillator means for providing pressure oscillations in oxygen flow and piezoelectric means connected to said fluid oscillator means so as to be responsive to said pressure oscillations by generation of electric energy.

5. In apparatus of claim 1, said time control means comprising a fluid bistable flip flop element means of low frequency, said on/off valve means being actuated by gas pressure output of said flip flop element means, said fluidic element having gas inlet means interconnected to said oxygen supply conduit and gas outlet means interconnected to said delivery conduit.

6. In apparatus of claim 5, said bistable flip flop element means comprising a proportional fluidic amplifier with positive feedback.

7. In apparatus of claim 6, said time interval adjustment means comprising flapper nozzle diaphragm assemblies, wherein nozzle to diaphragm distance adjustment determines time interval.

8. In apparatus of claim 2, said gas flow regulator means including: a plurality of flow restrictive elements of progressively greater restriction; flow selection means connected to said elements to select and insert a particular one of said elements in the gas flow path to select a particular gas flow rate; and gas supply indicator means connected to said flow selection means to indicate how long a particular gas supply will last at a particular flow rate.

9. Apparatus for conserving oxygen by providing, sequentially and repetitively, an ON time period and OFF time period of measured flow of supplemental oxygen gas from an oxygen supply conduit and through a delivery conduit to a spontaneously breathing patient which is supplemental to said patient's normal ambient air intake for improved function in certain disorders, as exemplified by chronic obstructive pulmonary disease, according to a program based upon such patient's characteristics relative to saturation time and desaturation time in said patient's use of such oxygen, comprising in combination:

automatically operated on/off valve means connected in said supply conduit for providing a flow of oxygen therethrough for a first, or ON time period and to provide said supplemental oxygen to said patient substantially at atmospheric pressure without substantially obstructing ambient air intake and to prevent said flow for a second, or OFF time period to conserve said oxygen gas;

time control means operatively connected to said valve means to actuate said valve means in accordance with said program, including independently adjustable ON time interval adjustment means and OFF time interval adjustment means, wherein each said time interval is independent of the patient's respiratory cycle, extends over a plurality of respiratory cycles, and is preset; and including means to operate said valve means and said time control means with energy derived from the expanding and flowing oxygen gas, said time control means comprising a bistable oscillator including: a first chamber closed by a first diaphragm means; a second chamber closed by a second diaphragm means, said chambers having gas inlet means interconnected to said oxygen supply conduit and gas outlet valve means interconnected to said delivery conduit; control member means operatively connected to both of said diaphragm means, and responsive to deflection of said diaphragm means by generally linear motion in one direction, said control member moving in a first sense when gas outlet valve means of said first chamber is closed and increasing pressure therein from gas entering via gas inlet means causes outward deflection of said first diaphragm means and said control member means moving in a second sense when gas outlet valve means of said second chamber is closed and increasing pressure therein causes outward deflection of said second diaphragm means; toggle means operatively connected to said control member means to store energy from motion of said control member means up to a critical position and then release said energy into a force moving said control member to impart a bistable character to said motion; connecting means operatively connecting both of said gas outlet valve means to said control member means so as to alternately open said gas outlet valve means in said first chamber when said gas outlet valve means in said second chamber is closed and to open said gas outlet valve means in said chamber when said gas outlet valve means in said first chamber is closed; and said control member means is operatively connected to said valve means to turn valve on by motion in a first sense and off by motion in a second sense.

10. In apparatus of claim 9, said connecting means comprising bistable connecting means between said gas outlet valve means and said control member means which maintains said gas outlet valve means closed during a first portion of the opening motion of said control member means and then abruptly opens wide said valve means when a critical point in said motion has been reached, thereby contributing to the bistable oscillation function.

11. Apparatus of claim 10 including spring means connected to said bistable connecting means for energy storage.

12. In apparatus of claim 9, chamber volume adjusting means in said chambers, said chamber volume adjusting means providing said independently adjustable time interval adjustment means.

13. Apparatus of claim 9, including spring means connected to, and compressed by, said toggle means for energy storage.

14. Apparatus of claim 9, wherein a single common diaphragm means closes both chambers and said toggle means is provided by the spring action in a non-planar diaphragm means.

15. Apparatus of claim 14, wherein the inlet means and gas outlet valve means of one of said chambers are connected to room air.

16. Apparatus of claim 9, wherein the inlet means and gas outlet valve means of one of said chambers are connected to room air.

* * * * *